United States Patent [19]

Naito et al.

[11] 4,231,928
[45] Nov. 4, 1980

[54] ANTIBACTERIAL AGENTS

[75] Inventors: Takayuki Naito, Kawasaki; Jun Okumura, Yokohama; Hajime Kamachi, Ichikawa, all of Japan

[73] Assignee: Bristol-Myers Company, New York, N.Y.

[21] Appl. No.: 32,837

[22] Filed: Apr. 24, 1979

Related U.S. Application Data

[63] Continuation-in-part of Ser. No. 839,687, Oct. 5, 1977, abandoned, which is a continuation-in-part of Ser. No. 784,904, Apr. 5, 1977, abandoned.

[51] Int. Cl.³ .................. C07D 499/66; C07D 499/68; C07D 499/70
[52] U.S. Cl. ................................ 260/239.1; 424/251; 544/236
[58] Field of Search ..................... 260/239.1; 424/250, 424/251; 544/236

[56] References Cited

U.S. PATENT DOCUMENTS

| | | | |
|---|---|---|---|
| 3,320,240 | 5/1967 | Fosker et al. | 260/239.1 |
| 3,873,523 | 3/1975 | Doub et al. | 260/239.1 |
| 3,933,795 | 1/1976 | Disseinkotter et al. | 260/239.1 |
| 3,939,150 | 2/1976 | Murakami et al. | 260/239.1 |
| 3,945,995 | 3/1976 | Yamada et al. | 260/239.1 |
| 3,951,955 | 4/1976 | Tobiki et al. | 260/239.1 |
| 3,953,428 | 4/1976 | Murakami et al. | 260/239.1 |
| 3,954,733 | 5/1976 | Tobiki et al. | 260/239.1 |
| 3,992,371 | 11/1976 | Tobiki et al. | 260/239.1 |
| 4,081,545 | 3/1978 | Clayton | 260/239.1 X |

FOREIGN PATENT DOCUMENTS

| | | | |
|---|---|---|---|
| 836022 | 5/1976 | Belgium | 260/239.1 |
| 2312976 | 9/1973 | Fed. Rep. of Germany | 260/239.1 |
| 2191556 | 2/1974 | France | 260/239.1 |
| 1440216 | 6/1976 | United Kingdom | 260/239.1 |

OTHER PUBLICATIONS

Stanovnik et al., Tetrahedron Letters, No. 1, pp. 33–36, (1968).
Pollak et al., J. Org. Chem., vol. 36, No. 17, 2457–2462, (1971).

Primary Examiner—Natalie Trousof
Assistant Examiner—Vera C. Clarke
Attorney, Agent, or Firm—Richard R. Lloyd

[57] ABSTRACT

The penicillins of the formulae

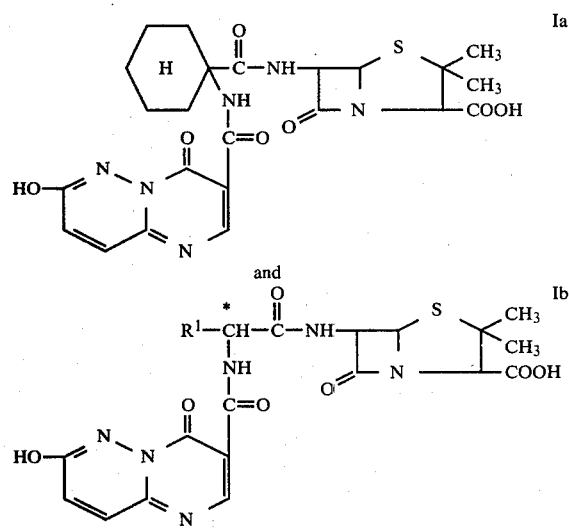

in which $R^1$ is phenyl, 2-thienyl, 3-thienyl, cyclohexyl, cyclohexen-1-yl, cyclohexa-1,4-dienyl, cyclohexa-1,4-dienylmethyl, 4-methoxycyclohexa-1,4-dienylmethyl or one of certain 4-substituted or 3,4-disubstituted phenyl moieties, and their pharmaceutically acceptable salts and physiologically hydrolyzed esters possess antibacterial activity and are particularly valuable in treating Pseudomonas infections.

16 Claims, No Drawings

ANTIBACTERIAL AGENTS

CROSS-REFERENCE TO RELATED APPLICATION

This application is a continuation-in-part of our prior co-pending application Ser. No. 839,687, filed Oct. 5, 1977 and now abandoned; which was a continuation-in-part of our prior co-pending application Ser. No. 784,904, filed Apr. 5, 1977, and now abandoned.

BACKGROUND OF THE INVENTION

1. Field of the Invention

The novel semi-synthetic penicillins of the present invention are useful as antibacterial agents for the treatment of bacterial infections caused by gram-positive and gram-negative bacteria including especially Pseudomonas strains.

2. Description of the Prior Art

It is well-known that penicillin antibiotics generally inhibit the growth of various gram-positive and gram-negative bacteria and are effective in the treatment of infections caused by these organisms. It is also known that few penicillins exert any appreciable antimicrobial activity against Pseudomonas. For the last two decades, however, the incidence of Pseudomonas aeruginosa infection has progressively increased. Recently, some penicillin antibiotics have been synthesized which are reported to be useful as antipseudomonal antibiotics (e.g. carbenicillin, U.S. Pat. No. 3,142,673; sulbenicillin, U.S. Pat. No. 3,660,379; and ticarcillin, U.S. Pat. No. 3,282,926), but these penicillins exhibit only a relatively low potency against Pseudomonas aeruginosa necessitating the use of large amounts of them for effective treatment. Therefore, there remains a need for the synthesis of new penicillins which possess a high degree of anti-Pseudomonas activity.

Various N-acyl derivatives of ampicillin (or a derivative thereof in which the phenyl ring is replaced by substituted phenyl, thienyl or another aryl or heterocyclic radical) have been disclosed in the patent and scientific literature. Illustrative patents and patent publications disclosing such derivatives containing an α-heterocycliccarboxamido group (where the heterocyclic ring may be bicyclic or polycyclic) are given below. Those publications which are limited to monocyclic heterocyclic groups are deemed less relevant and therefore are not included here.

(a) U.S. Pat. No. 3,945,995 disclosing penicillins of the formula

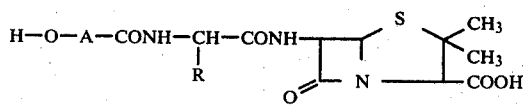

where R is an unsubstituted phenyl group or a substituted phenyl group having one or more hydroxyl groups or a cyclohexadienyl group and A represents a monocyclic or polycyclic nitrogen-containing heterocyclic aromatic ring. The 4-oxo-4H-pyrimido[1,2-b]pyridazin-3-yl moiety is not listed in the disclosure as being included within the definition of substituent "A", nor are any penicillins having such an "A" group illustrated or exemplified therein. (See also U.S. Pat. No. 4,005,075 having a substantially identical disclosure.)

(b) U.S. Pat. No. 3,953,428 disclosing ampicillin derivatives of the formula

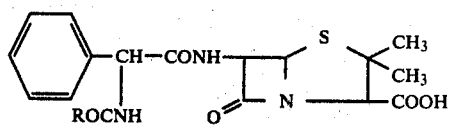

where R is selected from various nitrogen, sulfur or oxygen-containing mono-, bi- or polycyclic heterocyclic rings. The 4-oxo-4H-pyrimido[1,2-b]pyridazin-3-yl moiety is not included within the definition of substituent "R."

(c) U.S. Pat. No. 3,873,523 disclosing penicillins of the formula

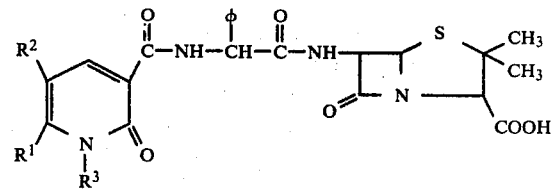

where $R^1$ is one of several named alicyclic, aryl or heterocyclic radicals, $R^2$ is hydrogen or, taken together with $R^1$ represents the group

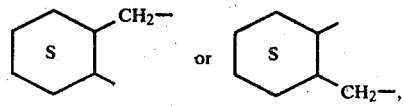

and $R^3$ is hydrogen or methyl. [See also U.S. Pat. No. 3,948,903, of which this is a divisional, having a similar disclosure.]

(d) U.S. Pat. No. 3,951,955 disclosing penicillins of the formula

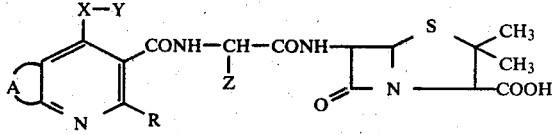

where A is a substituted or unsubstituted condensed aromatic carbocyclic or heterocyclic ring, R is hydrogen or lower alkyl, X is oxygen or sulfur, Y is hydrogen, lower alkyl, lower alkanoyl or lower alkoxycarbonyl and Z is phenyl or thienyl. (See also U.S. Pat. No. 3,864,329, of which 3,951,955 is a divisional, having a similar disclosure. Neither of these patents include the 4-oxo-4H-pyrimido[1,2-b]pyridazin-3-yl substituent within their scope.

(e) U.S. Pat. No. 3,954,733 disclosing penicillins of the formula

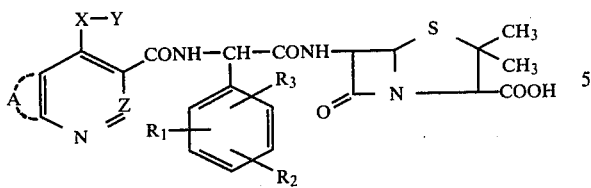

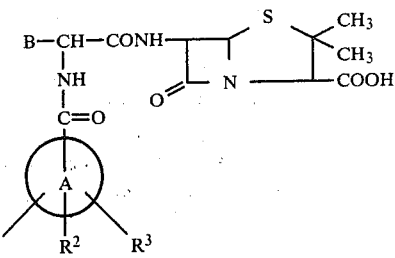

where A is a benzene ring or a 5 or 6-membered heteroaromatic ring containing 1 or 2 nitrogen atoms, Z is a nitrogen atom or a methylene group, X is an oxygen or sulfur atom, Y is hydrogen, lower alkoxycarbonyl or lower alkanoyl, $R_1$ is hydroxyl or protected hydroxyl and $R_2$ and $R_3$ are hydrogen or halogen. The 4-oxo-4H-pyrimido[1,2-b]pyridazin-3-yl substituent is not included within its scope.

(f) U.K. Pat. No. 1,440,216 disclosing compounds of the formula where B is a p-hydroxyphenyl or cyclohexadienyl, A is a 5- or 6-membered single or fused ring which may contain one or more nitrogen atoms, an oxygen atom or a sulfur atom and $R^1$, $R^2$ and $R^3$ each represent hydrogen, hydroxy, lower alkyl, nitro, halogen or an oxo group. No 4-oxo-4H-pyrimido-[1,2-b]pyridazin-3-yl "A" moieties are disclosed in this patent.

(i) French Patent Publication 2,191,556 (Farmdoc 23502U) disclosing penicillins of the formula

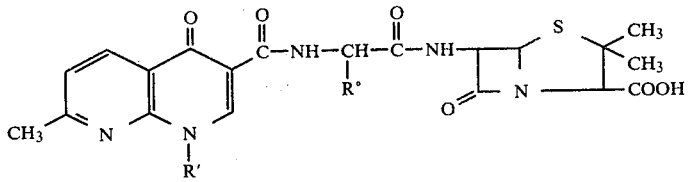

where R' is lower alkyl and R° is phenyl or chloro-substituted phenyl.

(j) U.S. Pat. No. 3,433,784 disclosing penicillins of the formula

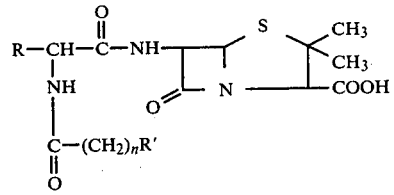

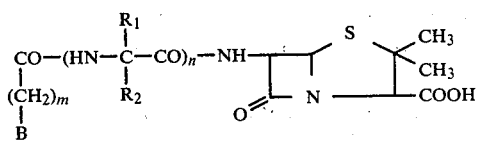

where $R_1$ is hydrogen and $R_2$ is optionally substituted phenyl, thienyl or furyl, n and m independently are 0 or 1 and B represents one of several named pyrimidyl radicals which do not include the 4-oxo-4H-pyrimido[1,2-b]pyridazin-3-yl moiety.

(g) U.S. Pat. No. 3,320,240 disclosing compounds of the formula where R is phenyl or thienyl, R' is optionally substituted heterocyclic and n is 0 or 1. No compounds are disclosed where n=0 and R' is a 4-oxo-4H-pyrimido[1,2-b]pyridazin-3-yl moiety.

(k) West German Published Application 2,312,976 (Farmdoc 59216U) disclosing penicillins of the formula

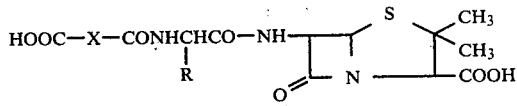

where R is an optionally substituted alkyl, aralkyl, aryl or heterocyclic group and X is a direct linkage or a divalent aliphatic, aromatic or heterocyclic radical which may be substituted. The 4-oxo-4H-pyrimido[1,2-b]pyridazin-3-yl moiety is not listed, illustrated or exemplified as a possible "X" substituent.

(h) U.S. Pat. No. 3,939,150 disclosing penicillins of the formula

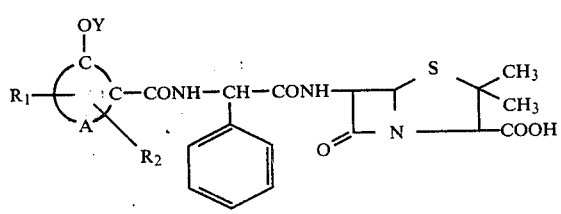

where

is a heteroaromatic ring with 6 ring atoms of which 1 or 2 are nitrogen atoms, Y is hydrogen, (lower)-alkanoyl or (lower)alkoxy-carbonyl, and $R_1$ and $R_2$ inter alia may be taken together to form a (lower)alkylene chain, optionally substituted with an oxo group.

(l) U.S. Pat. No. 3,933,795 disclosing inter alia penicillins of the formula

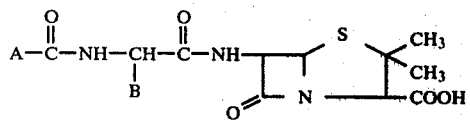

in which B is substituted or unsubstituted phenyl, thienyl, cyclohexen-1-yl or cyclohexa-1,4-dienyl, and "A" may be inter alia

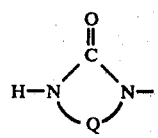

in which Q may be inter alia

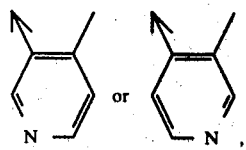

thus allowing "A" to be inter alia

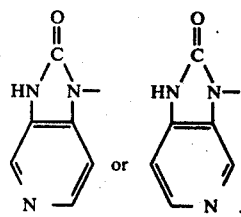

The extremely broad disclosure of "A" does not include the 4-oxo-4H-pyrimido[1,2-b]pyridazin-3-yl moiety, [See also U.S. Pat. Nos. 3,936,442, 3,939,149, 3,959,258, 3,972,869, 3,972,870, 3,974,140, 3,974,141, 3,974,142, 3,975,375, 3,978,056, 3,978,223, 3,980,792 and 3,983,105 having substantially the same disclosure.]

(m) U.S. Pat. No. 3,992,371 disclosing penicillins of the formula

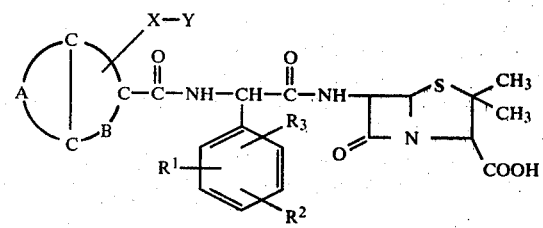

in which $R^1$, $R^2$ and $R^3$ are hydrogen or any of various named substituents,

represents inter alia a substituted or unsubstituted nitrogen-containing heteroaromatic ring,

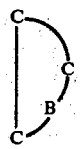

represents a pyridine, pyrazine or pyridazine ring, X is oxygen or sulfur, and Y is hydrogen, (lower)alkoxycarbonyl or (lower)alkanoyl. Although this disclosure encompasses numerous bicyclic heterocyclic groups, the 4-oxo-4H-pyrimido[1,2-b]pyridazin-3-yl moiety is not included therein. This is most easily seen by the fact that this patent discloses only bicyclic heterocyclic compounds in which both bridgehead atoms are carbon. In the novel compounds of the instant invention, one of the bridgehead atoms of the bicyclic heterocyclic group is nitrogen.

(n) Belgian Patent 836,022 (Farmdoc 46019X) disclosing inter alia penicillins of the formula

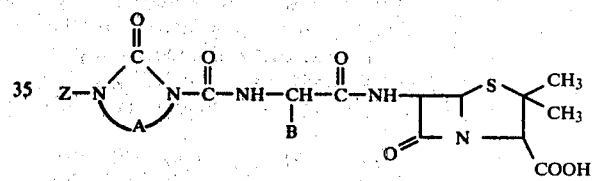

in which B may be substituted or unsubstituted phenyl, cyclohexenyl or cyclohexadienyl, A may be inter alia 1,2-phenylene, and Z is

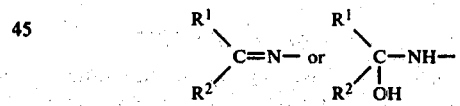

in which $R^1$ and $R^2$ may be hydrogen, alkyl cycloalkyl, aralkyl, aryl, heterocyclyl, COOH, CN, $NO_2$, $CONH_2$, etc., or $R^1$ and $R^2$ taken together may complete a 3-7 membered carbocyclic or heterocyclic ring. Thus, the closest teaching of this patent is to penicillins of the formula

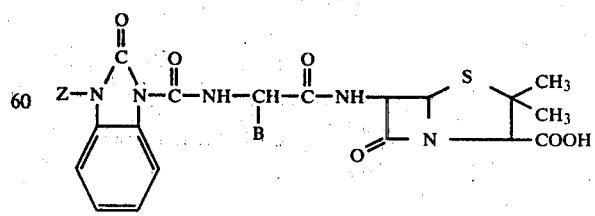

wherein B and Z are as defined above.

(o) U.S. Pat. No. 4,081,545 discloses penicillins of the formula

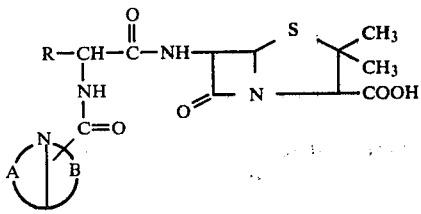

wherein R represents a furyl, thienyl, cycloalkyl, cycloalkenyl or phenyl group, or a phenyl group substituted by hydroxy, halogen, nitro, lower alkyl, lower alkoxy, amino or carboxy; and A and B are the same or different and each represents the residue of a substituted or unsubstituted fused 5- or 6-membered ring; and pharmaceutically acceptable non-toxic salts and in vivo hydrolyzable esters thereof. The patent names or shows the structure for numerous [4,4,0] heterocyclic ring systems containing from 1 to 3 nitrogens, [4,3,0] heterocyclic ring systems containing from 1 to 5 nitrogens, and [4,3,0] heterocyclic ring systems containing up to three nitrogens plus oxygen or sulfur. Although the 4-oxo-4H-pyrimido[1,2-b]pyridazin-3-yl ring system is one of the numerous heterocyclic ring systems depicted, there is no disclosure whatever as to a method of preparing the 7-hydroxy-4-oxo-4H-pyrimido[1,2-b]pyridazin-3-ylcarboxylic acid or the corresponding acid halide. Further, the patent teaches that ring A preferably is 5-membered.

(p) Tetrahedron Letters, (1), 33–36 (1968) discloses the preparation of 3-carbethoxypyrimido[1,2-b]-pyridazin-4-one, but there is no disclosure of a means of preparing the 7-hydroxy-4-oxo-4H-pyrimido[1,2-b]pyridazin-3-ylcarboxylic acid or the corresponding acid halide.

(q) J. Organic Chemistry, 36, 2457–2462 (1971) discloses the preparation of 3-carbethoxypyrimido[1,2-b]-pyridazin-4-one and 3-carbethoxy-7-chloropyrimido[1,2-b]-pyridazin-4-one, but there is no disclosure of a means of preparing the 7-hydroxy-4-oxo-4H-pyrimido[1,2-b]pyridazin-3-ylcarboxylic acid or the corresponding acid halide.

SUMMARY OF THE INVENTION

The present invention comprises certain novel penicillin derivatives, methods for preparation of said derivatives and pharmaceutical compositions comprising as the active ingredient(s), either (a) one of said penicillin derivatives or (b) one of said penicillin derivatives in combination with amikacin (1-[L-(−)-α-amino-α-hydroxybutryl]-kanamycin (A) or a pharmaceutically acceptable acid addition salt thereof. More particularly, the present invention provides the novel penicillin derivatives having the formulae

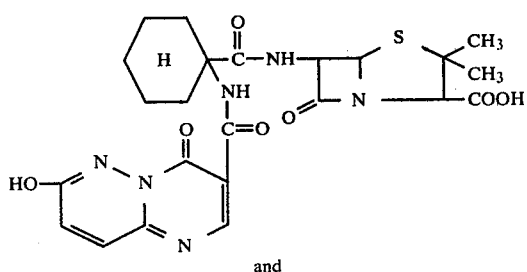

and

-continued

Ib in which $R^1$ is and their pharmaceutically acceptable salts and conventional physiologically hydrolyzed esters including especially the pivaloyloxymethyl, acetoxymethyl, methoxymethyl, phthalidyl and indanyl esters.

The pharmaceutically acceptable salts referred to above include nontoxic metallic salts such as sodium, potassium calcium and magnesium, the ammonium salt and substituted ammonium salts, e.g. salts of such nontoxic amines as trialkylamines (e.g. triethylamine), procaine, dibenzylamine, N-benzyl-β-phenethylamine, 1-ephenamine, N,N'-dibenzylethylenediamine, dehydroabietylamine, N,N'-bis(dehydroabietyl)ethylenediamine, N-(lower)alkyl-piperidine (e.g. N-ethylpiperidine) and other amines which have been used to form pharmaceutically acceptable salts of penicillins and cephalosporins. The most preferred salts are the alkali metal salts, i.e. the sodium and potassium salts.

As used herein the term "physiologically hydrolyzed esters" refers to those pharmaceutically acceptable esters (of penicillins or cephalosporins) known in the art to hydrolyze to the free acid form in vivo. Esters of this type are described, for example, in U.S. Pat. Nos. 3,859,274, 3,860,570, 3,860,579, 3,864,331, 3,873,521 and 3,919,196, in U.K. Patent Specifications 1,215,812, 1,267,936, 1,425,571, and 1,400,584, and in German Published Applications 1,951,012 and 2,230,620. Examples of suitable physiologically hydrolyzed esters include acetoxymethyl, pivaloyloxymethyl, α-acetoxyethyl, α-acetoxybenzyl, α-pivaloyloxyethyl, phthalidyl(3-phthalidyl), indanyl(5-indanyl), methoxymethyl, benzoyloxymethyl, α-ethyl-butyryloxymethyl, propionyloxymethyl, valeryloxymethyl and isobutyryloxymethyl. The preferred esters are the acetoxy-methyl, pivaloyloxymethyl, methoxymethyl, phthalidyl and 5-indanyl esters, most preferably acetoxymethyl, methoxymethyl and pivaloyloxymethyl.

Included within the scope of this invention are the optically active isomeric forms and mixtures thereof which arise by virtue of the asymmetric α-carbon atom in the 6-acyl side chain of Compounds Ib, i.e. the asterisked carbon atom shown in formula Ib above. These are the D-and L-epimers and the DL-form which is a mixture of the two optically active isomers. The D-form of the compounds of the present invention is the preferred form because of it greater activity relative to that of the L- or the DL-forms.

DETAILED DESCRIPTION OF THE INVENTION

The novel and valuable penicillins of formula Ia and Ib may be prepared according to one procedure by reacting a compound of the formula

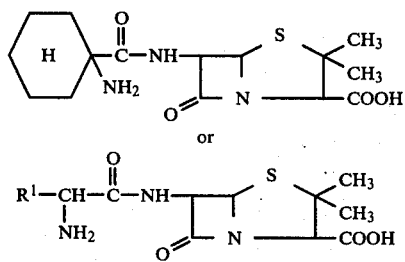

(preferably, with respect to the compounds of formula IIb, a compound having the D-configuration in the 6-side chain or a salt or easily cleavable ester thereof with an acylating agent of the formula

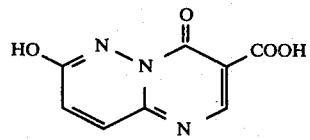

or with a reactive acylating derivative thereof and, if the reaction product contains an easily cleavable ester protecting group, optionally removing said protecting group by a method known per se and, if desired, converting by a method known per se (a) the product in the form of a free acid to a pharmaceutically acceptable salt or a physiologically hydrolyzed ester thereof, or (b) the product in the form of a salt to the free acid or a pharmaceutically acceptable salt or a physiologically hydrolyzed ester thereof. The above acylation reaction may be carried out by methods which are themselves known in the art, e.g. from the synthesis of peptides, penicillins and cephalosporins.

The starting material penicillins of formula IIa and IIb are known compounds. Preparation of the acylating acid starting material III is described below.

In the acylationn of the α-amino group of penicillin IIa or IIb, the carboxylic acid of formula III may be used per se in which case it is preferred to use an enzyme or a condensing agent. Suitable condensing agents include N,N'-dimethylchloroformiminium chloride, an N,N'-carbonyldiimidazole or an N,N'-carbonylditriazole, a carbodiimide reagent (especially N,N'-dicyclohexylcarbodiimide, N,N'-diisopropylcarbodiimide or N-cyclohexyl-N'-(2-morpholinoethyl)carbodiimide, alkylylamine reagent, an isoxasolium salt reagent, ketenimine reagent, hexachlorocyclotriphosphatriazine or hexabromocyclotriphosphatriazine, diphenylphosphoryl azide (DPPA), diethylphosphorylcyanide (DEPC), diphenylphosphite or N-ethoxycarbonyl-2-ethoxy-1,2-dihydroquinoline (EEDQ).

As an alternative to using the carboxylic acid III in the above process, there may also be employed reactive acylating derivatives of acid III, i.e. functional equivalents of the acid as acylating agents for a primary amino group. Examples of reactive acylating derivatives of the carboxylic acid include the acid halide (e.g. acid chloride or acid bromide), acid anhydrides, including mixed anhydrides (e.g. alkoxyformic anhydrides), acid azides, active esters (e.g. p-nitrophenyl) and active thioesters. Another reactive derivative of the acid is a corresponding azolide, i.e. an amide of the acid whose amide nitrogen is a member of a quasiaromatic five-membered ring containing at least two nitrogen atoms, i.e. imidazole, pyrazole, the triazoles, benzimidazole, benzotriazole and their substituted derivatives. The general method for preparation of azolides is described, for example, in U.S. Pat. No. 3,910,900.

Mention was made above of the use of enzymes to couple the free acid with compound II. Included in the scope of such processes are the use of an ester, e.g. the methyl ester, of that free acid with enzymes provided by various microorganisms, e.g. those described in *J. Am. Chem. Soc.*, 94(11), 4035–4037 (1972), *M. Antibiotics (Japan)*, 24(5), 321–323 (1971) and U.S. Pat. No. 3,682,777.

Acylation with the carboxylic acid III or reactive acylating derivative thereof may be carried out on the penicillanic acid of formula IIa or IIb or a salt (e.g. an alkali metal or an amine salt) or easily cleavable ester thereof.

The term "easily cleavable ester" refers to a derivative of the penicillanic acid in which the 3-carboxyl group has been protected by any of the known ester protective groups capable of being removed following the acylation reaction by methods, e.g. chemical or enzymatic hydrolysis, treatment with chemical reducing agents under mild conditions, irradiation with ultraviolet light or catalytic hydrogenation, which do not result in any appreciable destruction of the remaining portion of the molecule. Examples of suitable "easily cleavable esters" include trialkylsilyl (e.g. trimethylsilyl) and other esters derived from silyl alcohol or stannyl alcohol which can be removed by solvolysis with a solvent containing hydroxyl groups, t-butoxycarbonyl, benzhydryl, benzyl, p-nitrobenzyl, p-methoxybenzyl, 2,2,2-trichloroethyl, phenacyl, acetonyl, p-bromophenacyl, (lower)alkyl such as methyl, ethyl or t-butyl and the physiologically hydrolyzed esters mentioned above. The general methods for the preparation of these esters and for their removal are described in the literature and are well-known to those skilled in the art.

The acylation process is conducted in a reaction-inert solvent system which can be aqueous or non-aqueous. Suitable reaction-inert solvents include, for example, water, acetone, tetrahydrofuran, dioxane, acetonitrile, dimethylformamide, dimethylsulfoxide, methylene chloride, chloroform, benzene, toluene, methyl isobutyl ketone and mixtures of the above-mentioned organic solvents with water. The choice of solvent, i.e. particularly whether an aqueous or non-aqueous solvent is used, is dependent on the particular starting materials employed. Thus, for example, if the penicillin starting material IIa or IIb is used in the form where the 3-carboxyl moiety is protected by an ester group cleaved by hydroxylic solvents, e.g. a silyl or stannyl esters, an aprotic organic solvent is most preferably employed. Also, when the penicillin of formula IIa or IIb is used in its salt form, water or an aqueous organic solvent system is preferably employed. The most advantageous solvent system for the particular reagents used can be determined by routine experimentation.

The duration and temperature of the acylation reaction are not critical. Temperatures in the range of from about −30° C. to about +50° C. are commonly used for reaction times ranging from less than one hour up to a day or more. Although the initial contacting of the reactants is preferably carried out at around 0° C. to reduce the incidence of by-products, it is frequently desirable after a few minutes of mixing to allow the reaction mixture to warm to room temperature until the reaction is complete.

The reactants of formulae II and III are normally employed in approximate equimolar quantities, although an excess of either can be used if desired.

When a carboxyl-protecting group is present in the product of the acylation reaction, it may be eliminated, if desired, in a per se conventional manner to give the desired 3-carboxylic acid penicillin or a salt thereof.

The acylation product is isolated in a conventional manner as the free acid or as a salt or as a physiologically hydrolyzed ester (if the appropriate ester group has been used in the acylation process). The free acid can be converted to a pharmaceutically acceptable salt thereof by treatment with an appropriate organic or inorganic base. The carboxylate salts may be converted to the free acids by treatment with an acid or suitable ion exchange resin. The product in the form of the free acid or salt thereof may also be converted by known methods to a corresponding physiologically hydrolyzed ester such as the pivaloyloxymethyl, acetoxymethyl, phthalidyl, 5-indanyl or methoxymethyl esters.

An alternative process for preparing the penicillins of formula Ia and Ib comprises reacting 6-aminopenicillanic acid or a salt or easily cleavable ester thereof with an acylating agent of the formula

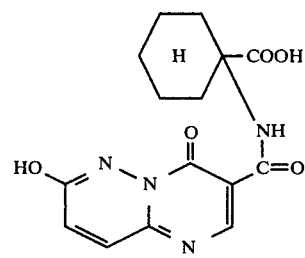

IVa

-continued
or

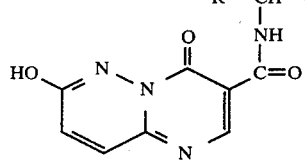

IVb in which $R^1$ is as defined above (preferably, in the case of a compound of formula IVb, having the D-configuration at the α-carbon atom), or a reactive acylating derivative thereof and, if the reaction product contains an easily cleavable ester protecting group, optionally removing said protective group by a method known per se and, if desired, converting by methods known per se (a) the product in the form of a free acid to a pharmaceutically acceptable salt or a physiologically hydrolyzed ester thereof, or (b) the product in the form of a salt to the free acid or a pharmaceutically acceptable salt or a physiologically hydrolyzed ester thereof.

The terms "easily cleavable ester," "reactive acylating derivative," "pharmaceutically acceptable salt" and "physiologically hydrolyzed ester" used above in the description of the alternative process are as defined previously.

The acylation conditions, i.e. solvents, temperatures, molar ratios and isolation procedures, for this process are substantially the same as those described in connection with the first-mentioned process.

Carboxylic acid starting materials IVa and IVb may be prepared by the reaction of a compound of the formula

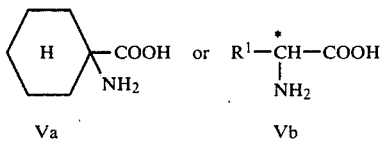

Va   Vb (preferably, in the case of a compound of formula Vb, having the D-configuration), with the carboxylic acid of formula III or a reactive acylating derivative thereof in substantially the same manner as that for the other acylation steps described above.

The penicillins provided by the present invention are useful as antimicrobial agents against various gram-positive and gram-negative bacteria including especially Pseudomonas and may be used in the same manner as other commercially available penicillins such as ampicillin or amoxicillin. In the treatment of bacterial infections in man, the compounds of this invention are preferably administered parenterally in an amount of from about 15 to 150 mg./kg./day in divided dosage, e.g. 3 to 4 times a day. They are administered in dosage units containing, for example, 125, 250 or 500 mg. of active ingredient, with suitable physiologically acceptable carriers or diluents. The dosage units are preferably in the form of liquid preparations such as solutions or suspensions.

The compounds of the present invention have been found to be particularly effective against Pseudomonas organisms. As of today, two standard commercially available penicillins used against Pseudomonas infections are sulbenicillin and carbenicillin. As demonstrated below, the penicillins of the present invention are more active against Pseudomonas strains than either sulbenicillin or carbenicillin.

The Minimum Inhibitory Concentrations (MIC) for sodium 6-[D-(−)-α-phenyl-α-(7-hydroxy-4-oxo-4H-pyrimido[1,2-b]pyridazin-3-ylcarboxamido)acetamido]-penicillanate (BB-P598) and sulbenicillin were determined by the serial twofold agar dilution method using Steers' apparatus on Mueller-Hinton agar plates against 31 test organisms for the primary screening (Table 1) and also against 61 strains of *Pseudomonas aeruginosa* for the secondary evaluation (Table 2).

Against most of the 6 strains of S. aureus and the Gram-negative organisms except Pseudomonas (19 strains), BB-P598 was equal to or less active than sulbenicillin, while, against Pseudomonas it was significantly more active than sulbenicillin. In terms of mean % relative activity to sulbenicillin, BB-P598 was 713% more active than sulbenicillin against the 6 strain of Pseudomonas in Table 1 and 756% more active against the 61 Pseudomonas strains of Table 2.

TABLE 1

In Vitro Activity By Agar Dilution Technique (Mueller-Hinton Agar).

| Organism | | MIC (mcg/ml) BB-P598 | Sulbenicillin |
|---|---|---|---|
| S. aureus Smith | A9537 | 1.6 | 1.6 |
| S. aureus Smith | A20239 | 25 | 6.3 |
| S. aureus BX-1633 | A9606 | 6.3 | 6.3 |
| S. aureus BX-1633 | A15097 | 100 | 12.5 |
| S. aureus BX-1633 | A20240 | 6.3 | 6.3 |
| S. aureus BX-1633 | A20701 | >100 | 50 |
| E. coli NIHJ | | 0.8 | 0.8 |
| E. coli Juhl | A15119 | 12.5 | 3.1 |
| E. coli Juhl | A9844 | 3.1 | 0.8 |
| E. coli Juhl | A20664 | 0.8 | 3.1 |
| E. coli Juhl | A20366 | >100 | >100 |
| E. coli Juhl | A9435 | 12.5 | 12.5 |
| E. coli Juhl | A20898 | >100 | >100 |
| E. coli Juhl | A20732 | 100 | >100 |
| E. coli Juhl | A20520 | 1.6 | 6.3 |
| K. pneumoniae | A9977 | 12.5 | 3.1 |
| Klebsiella sp. | A20452 | 25 | 12.5 |
| E. cloacae | A9656 | 25 | 6.3 |
| E. cloacae | A9657 | 50 | 100 |
| E. cloacae | A9659 | 25 | 12.5 |
| P. mirabilis | A9900 | 0.2 | 0.8 |
| P. vulgaris | A9539 | 25 | 1.6 |
| P. morganii | A9553 | >100 | >100 |
| S. enteritidis | A9531 | 6.3 | 1.6 |
| S. marcescens | A20019 | 100 | 6.3 |
| P. aeruginosa | A9930 | 1.6 | 12.5 |
| P. aeruginosa | A15150 | 0.8 | 12.5 |
| P. aeruginosa | A9843 | 3.1 | 25 |
| P. aeruginosa | A20717 | 6.3 | 100 |
| P. aeruginosa | A20229 | 1.6 | 12.5 |
| Pseudomonas sp. | A20358 | 1.6 | 3.1 |

TABLE 2

In vitro Activity By Agar Dilution Technique Against 61 Strains Of *Pseudomonas aeruginosa* (Mueller-Hinton Agar)

| BBRI Code # | Organism | | | MIC (mcg/ml) BB-P598 | Sulbenicillin |
|---|---|---|---|---|---|
| Pa-1 | P. aeruginosa | D15 | | 6.3 | 25 |
| Pa-2 | P. aeruginosa | VA | A9923 | 3.1 | 12.5 |
| Pa-3 | P. aeruginosa | 1449VA | A9930 | 1.6 | 6.3 |
| Pa-4 | P. aeruginosa | H9 D113 | A21295 | 6.3 | 25 |
| Pa-5 | P. aeruginosa | M4865KC | A15150 | 3.1 | 25 |
| Pa-6 | P. aeruginosa | No. 5 | A15194 | 25 | >100 |
| Pa-7 | P. aeruginosa | | A9843 | 6.3 | 25 |
| Pa-8 | P. aeruginosa | | A9843A | 3.1 | 25 |
| Pa-9 | P. aeruginosa | Yale | | 3.1 | 25 |
| Pa-10 | P. aeruginosa | | A20479 | >100 | >100 |
| Pa-11 | P. aeruginosa | | A20616 | 3.1 | 25 |
| Pa-12 | P. aeruginosa | | A20653 | 6.3 | 50 |
| Pa-14 | P. aeruginosa | | A20325 | 3.1 | 25 |
| Pa-15 | P. aeruginosa | | A20717 | 6.3 | 100 |
| Pa-16 | P. aeruginosa | #130 | A20718 | 0.8 | 6.3 |
| Pa-17 | P. aeruginosa | H6 D114 | | 3.1 | 12.5 |
| Pa-18 | P. aeruginosa | H8 D121 | | 3.1 | 12.5 |
| Pa-19 | P. aeruginosa | | A20229 | 1.6 | 12.5 |
| Pa-20 | P. aeruginosa | | A20325 | 6.3 | 25 |
| Pa-21 | P. aeruginosa | | A20601 | 3.1 | 25 |
| Pa-23 | P. aeruginosa | | A20741 | 6.3 | 50 |
| Pa-24 | P. aeruginosa | | A20896 | 25 | 100 |
| Pa-25 | P. aeruginosa | | A20897 | 1.6 | 12.5 |
| Pa-26 | P. aeruginosa | Ps32 | | 1.6 | 12.5 |
| Pa-27 | P. aeruginosa | GN315 | A21294 | 3.1 | 50 |
| Pa-28 | P. aeruginosa | CPH10527/72 | | 6.3 | 50 |
| Pa-29 | P. aeruginosa | D122 | | 3.1 | 25 |
| Pa-30 | P. aeruginosa | | A20600 | 3.1 | 25 |
| Pa-31 | P. aeruginosa | | A20594 | 0.8 | 12.5 |
| Pa-32 | P. aeruginosa | | A20595 | 3.1 | 25 |
| Pa-33 | P. aeruginosa | | A20598 | 12.5 | 100 |
| Pa-34 | P. aeruginosa | | A20603 | 3.1 | 25 |
| Pa-35 | P. aeruginosa | | | 12.5 | 100 |
| Pa-36 | P. aeruginosa | | | 0.4 | 1.6 |
| Pa-37 | P. aeruginosa | | A20130 | 3.1 | 50 |
| Pa-38 | P. aeruginosa | | A20349 | 6.3 | 50 |
| Pa-39 | P. aeruginosa | | A20641 | 3.1 | 25 |
| Pa-41 | P. aeruginosa | | A21227 | 3.1 | 25 |
| Pa-42 | P. aeruginosa | | A21229 | 25 | >100 |
| Pa-43 | P. aeruginosa | | A21233 | 3.1 | 50 |

TABLE 2-continued

In vitro Activity By Agar Dilution Technique Against 61 Strains Of *Pseudomonas aeruginosa* (Mueller-Hinton Agar)

| BBRI Code # | Organism | | | MIC (mcg/ml) BB-P598 | Sulbenicillin |
|---|---|---|---|---|---|
| Pa-44 | P. aeruginosa | | A21274 | 3.1 | 50 |
| Pa-45 | P. aeruginosa | GN4925 | | 6.3 | 50 |
| Pa-51 | P. aeruginosa | | A9910 | 3.1 | 25 |
| Pa-52 | P. aeruginosa | | A9926 | 3.1 | 25 |
| Pa-53 | P. aeruginosa | | A20126 | 3.1 | 25 |
| Pa-54 | P. aeruginosa | | A20128 | 3.1 | 50 |
| Pa-55 | P. aeruginosa | | A20227 | 3.1 | 25 |
| Pa-56 | P. aeruginosa | | A20228 | 3.1 | 25 |
| Pa-57 | P. aeruginosa | | A20546 | 3.1 | 25 |
| Pa-58 | P. aeruginosa | | A20557 | 6.3 | 50 |
| Pa-59 | P. aeruginosa | | A20574 | 6.3 | 50 |
| Pa-60 | P. aeruginosa | | A20602 | 1.6 | 12.5 |
| Pa-61 | P. aeruginosa | | A20726 | 6.3 | 50 |
| Pa-62 | P. aeruginosa | | A21213 | 12.5 | >100 |
| Pa-64 | P. aeruginosa | | A21336 | 3.1 | 25 |
| Pa-65 | P. aeruginosa | | A21428 | 1.6 | 25 |
| Pa-66 | P. aeruginosa | | A21434 | 3.1 | 25 |
| Pa-67 | P. aeruginosa | | A21509 | 6.3 | 50 |
| Pa-68 | P. aeruginosa | | A21510 | 6.3 | 50 |
| Pa-69 | P. aeruginosa | | A21587 | 12.5 | 50 |
| Pa-70 | P. aeruginosa | K-Ps102 | (CR-102) | 3.1 | 25 |
| Geometric mean of MIC | | | | 4.2 | 31.4 |
| Mean % relative activity (sulbenicillin = 100%) | | | | 756 | 100 |

The MIC's of BB-P598 against various organisms were also determined by the tube dilution method (Nutrient broth), and the results, compared with sulbenicillin, are shown in Table 3.

TABLE 3

In vitro Activity By Tube Dilution Method (Nutrient Broth)

| | Organism | | MIC (mcg./ml.) BB-P598 | Sulbenicillin |
|---|---|---|---|---|
| Dp-4 | D. pneumoniae | A9585 | 0.01 | 0.08 |
| Sp-3 | S. pyogenes | A9604 | 0.08 | 0.31 |
| Sa-2 | S. aureus Smith | A9537 | 3.1 | 3.1 |
| Sa-2 | S. aureus Smith +50% serum | | 1.6 | 3.1 |
| Sa-11 | S. aureus BX-1633 | A9606 | 50 | 12.5 |
| Sa-44 | S. aureus | A15097 | 100 | 25 |
| Se-1 | S. enteritidis | A9531 | 3.1 | 1.6 |
| Ec-1 | E. coli NIHJ | | 6.3 | 6.3 |
| Ec-3 | E. coli Juhl | A15119 | 25 | 25 |
| Ec-58 | E. coli | A9675 | 50 | 100 |
| Kp-3 | K. pneumoniae | A9977 | 12.5 | 6.3 |
| Kp-4 | K. pneumoniae | A15130 | >100 | >100 |
| Pm-2 | P. mirabilis | A9900 | 6.3 | 0.8 |
| Pg-8 | P. morganii | A15153 | >100 | 12.5 |
| Sm-1 | S. marcescens | A20019 | 50 | 25 |
| El-1 | E. cloacae | A9656 | 100 | 50 |
| Pa-13 | P. aeruginosa | A9843 | 6.3 | 25 |
| Pa-19 | P. aeruginosa | A20229 | 6.3 | >100 |
| Pa-57 | P. aeruginosa | A20546 | 3.1 | 25 |

The effect of inoculum size of the MIC and MBC (Minimum Bacteriacidal Concentration) of BB-P598 against *P. aeruginosa* A9843 also was determined. The MIC's were determined by the serial tube dilution method in Nutrient Broth using four levels of inoculum size ($5.3 \times 10^3$, $5.3 \times 10^4$, $5.3 \times 10^5$ and $5.3 \times 10^6$ cells/ml), along with sulbenicillin as a reference standard. The results are shown in Table 4.

TABLE 4

Effect Of Inoculum Size on MIC (Nutrient Broth) Against *P. aeruginosa* A9843

| | MIC (mcg/ml) | | | | MIC ratio | |
|---|---|---|---|---|---|---|
| | $5.3 \times 10^3$ cell/ml | $5.3 \times 10^4$ (a) | $5.3 \times 10^5$ (b) | $5.3 \times 10^6$ (c) | b/a | c/a |
| BB-P598 | 6.3 | 12.5 | >25 | >100 | 2 | >8 |
| Sulbenicillin | 25 | 50 | >200 | >400 | 4 | >8 |

Subsequent to the above MIC determinations, aliquots from the non-turbid tubes were added to Nutrient Agar plates to determine the MBC value. The MBC was assigned to the lowest concentration which killed 99% of the original cell population. The results of these tests at two levels of inoculum size ($5.3 \times 10^3$ and $5.3 \times 10^4$ cells/ml), along with the MBC/MIC ratios are shown in Table 5.

TABLE 5

Effect Of Inoculum Size On MBC and MBC/MIC Ratio Against *P. Aeruginosa* A9843

| | Inoculum size, cell/ml | | | | | |
|---|---|---|---|---|---|---|
| | $5.3 \times 10^3$ | | | $5.3 \times 10^4$ | | |
| | MIC mcg/ml | MBC mcg/ml | MBC/ MIC | MIC mcg/ml | MBC mcg/ml | MBC/ MIC |
| BB-P598 | 6.3 | 50 | 8 | 12.5 | >100 | >8 |
| Sulbenicillin | 25 | 100 | 4 | 50 | 200 | 4 |

Mouse blood levels of BB-P598 and BB-P642 were determined by subcutaneous administration of 20 mg/kg of the penicillin to groups of three mice. Blood samples collected from orbital sinuses were assayed by the paper disk agar-diffusion method on *Sarcina lutea* PC1 1001 plates. The results are shown in Table 6.

TABLE 6

Mouse Blood Levels (mcg/ml) After Single Dose of 20 mg/kg Subcutaneously (average of 3 mice)

| Time | BB-P598 | BB-P642 | Sulbenicillin | Carbenicillin |
|---|---|---|---|---|
| 15 min. | 3.57 | 18 | 9.8 | 11.5 |
| 30 min. | 0.9 | 13.5 | 7.5 | 9 |
| 60 min. | — | 5.2 | 1.2 | 5.8 |

BB-P598 was evaluated in vivo in experimental infections in mice. The pathogenic bacteria employed were *P. aeruginosa* A9843, *E. coli* Juhl and *S. aureus* Smith. Mice were challenged intraperitoneally with a $100 \times LD_{50}$ dose of the pathogens in a 5% suspension of hog gastric mucin. The penicillin was administered subcutaneously as a single treatment, just after the bacterial challenge. The results of this test are shown in Table 7.

TABLE 7

In Vivo Activity In Mice (Survival/Tested)

| Dose of Penicillin (sc) | BB-P598 | Sulbenicillin |
|---|---|---|
| (a) *P. aeruginosa* A9843 | | |
| 400 mg/kg | — | 4/5 |
| 100 | 3/5 | 2/5 |
| 25 | 1/5 | 0/5 |
| 6.3 | 1/5 | 0/5 |
| 1.6 | 0/5 | 0/5 |
| PD$_{50}$ (mg/kg) | 54 | 140 |
| MIC (mcg/ml) | 6.3 | 25 |
| (b) *E. coli* Juhl | | |
| 100 mg/kg | 3/5 | 5/5 |
| 25 | 2/5 | 5/5 |
| 6.3 | 1/5 | 1/5 |
| 1.6 | 0/5 | 0/5 |
| 0.4 | — | — |
| PD$_{50}$ (mg/kg) | 40 | 9.5 |
| MIC (mcg/ml) | 25 | 25 |
| (c) *S. aureus* Smith | | |
| 100 mg/kg | 5/5 | — |
| 25 | 5/5 | 5/5 |
| 6.3 | 5/5 | 5/5 |
| 1.6 | 0/5 | 0/5 |
| 0.4 | — | 0/5 |
| 0.1 | — | — |
| PD$_{50}$ (mg/kg) | 3.1 | 3.1 |
| MC (mcg/ml) | 3.1 | 6.3 |

PD$_{50}$ = Protective Dose$_{50}$, i.e. the dose required to give protection to 50% of the infected mice.

Minimum Inhibitory Concentrations (MIC) for sodium 6-[D-(—)-α-phenyl-α-(7-hydroxy-4-oxo-4H-pyrimido[1,2-b]pyridazin-3-ylcarboxamido)acetamido]-pencillanate (BB-P598), sodium 6-[D-(—)-α-(4-hydroxyphenyl)-α-(7-hydroxy-4-oxo-4H-pyrimido[1,2-b]pyridazin-3-ylcarboxamido)acetamido]-penicillanate (BB-P642) and carbenicillin were determined by the serial twofold agar dilution method using Steers' apparatus on Mueller-Hinton agar plates against 31 tests organisms (Table 8) and also against 61 strains of *Pseudomonas aeruginosa* (Table 9). In terms of mean % relative activity compared with carbenicillin, compounds BB-B598 and BB-P642 were 856% and 1319% as active as carbenicillin against the 61 Pseudomonas strains of Table 9.

TABLE 8

Vitro VitroActivity by Agar Dilution Technique (Mueller-Hinton Agar)

| | | MIC (mcg/ml) | | |
|---|---|---|---|---|
| Organisms | | BB-P598 | BB-P642 | carbenicillin |
| *S. aureus* Smith | A9537 | 1.6 | 3.1 | 0.2 |
| *S. aureus* | A20239 | 25 | 25 | 6.3 |
| *S. aureus* BX-1633 | A9606 | 50 | 25 | 6.3 |
| *S. aureus* | A15097 | >100 | >100 | 50 |
| *S. aureus* | A20240 | 12.5 | 12.5 | 3.1 |
| *S. aureus* | A20701 | >100 | >100 | 50 |
| *E. coli* NIHJ | | 3.1 | 3.1 | 0.4 |
| *E. coli* Juhl | A15119 | 12.5 | 6.3 | 3.1 |
| *E. coli* | A9844 | 6.3 | 3.1 | 0.4 |
| *E. coli* | A20664 | 0.8 | 1.6 | 0.8 |
| *E. coli* | A20366 | >100 | >100 | >100 |
| *E. coli* | A9635 | 12.5 | 12.5 | 6.3 |
| *E. coli* | A20898 | >100 | >100 | >100 |
| *E. coli* | A20732 | 50 | 100 | >100 |
| *E. coli* | A20520 | 3.1 | 6.3 | 1.6 |
| *K. pneumoniae* | A9977 | 12.5 | 6.3 | 3.1 |
| *Klebsiella sp.* | A20452 | 12.5 | 12.5' | 6.3 |
| *E. cloacae* | A9656 | 25 | 25 | 3.1 |
| *E. cloacae* | A9657 | 100 | 100 | 25 |
| *E. cloacae* | A9659 | 25 | 25 | 3.1 |
| *P. mirabilis* | A9900 | 6.3 | 3.1 | 0.4 |
| *P. vulgaris* | A9539 | 25 | 50 | 1.6 |
| *P. morganii* | A9553 | >100 | >100 | >100 |
| *S. enteritidis* | A9531 | 6.3 | 3.1 | 0.8 |
| *S. marcescens* | A20019 | 50 | >100 | 3.1 |
| *P. aeruginosa* | A9930 | 1.6 | 1.6 | 25 |
| *P. aeruginosa* | A15150 | 1.6 | 0.8 | 25 |
| *P. aeruginosa* | A9843 | 3.1 | 1.6 | 25 |
| *P. aeruginosa* | A20717 | 6.3 | 3.1 | 100 |
| | A20229 | 1.6 | 0.4 | 25 |
| *Pseudomonas sp.* | A20358 | 1.6 | 0.4 | 3.1 |

TABLE 9

In Vitro Activity By Agar Dilution Technique Against 61 Strains of *Pseudomonas aeruginosa* (Mueller-Hinton Agar)

| BBRI Code # | Organism | | | MIC (mcg/ml) BB-P 598 | BB-P 642 | Carbenicillin |
|---|---|---|---|---|---|---|
| Pa-1 | *P. aeruginosa* | D15 | | 6.3 | 1.6 | 12.5 |
| Pa-2 | " | V.A | A9923 | 3.1 | 1.6 | 25 |
| Pa-3 | " | 1449 V.A | A9930 | 3.1 | 1.6 | 12.5 |
| Pa-4 | " | H9, D113 | A21295 | 3.1 | 3.1 | 25 |
| Pa-5 | " | M4865, K.C | A15150 | 1.6 | 1.6 | 6.3 |
| Pa-6 | " | No. 5 Levitan | A15194 | 12.5 | 12.5 | >100 |
| Pa-7 | " | | A9843 | 3.1 | 1.6 | 50 |
| Pa-8 | " | | A9843A | 1.6 | 1.6 | 25 |
| Pa-9 | " | Yale | | 1.6 | 1.6 | 25 |
| Pa-10 | " | | A21479 | 100 | >100 | >100 |
| Pa-11 | " | | A20616 | 6.3 | 1.6 | 25 |
| Pa-12 | " | | A20653 | 6.3 | 1.6 | 50 |
| Pa-14 | " | ATCC 19660 | A20325 | 6.3 | 1.6 | 50 |
| Pa-15 | " | | A20717 | 12.5 | 6.3 | >100 |
| Pa-16 | " | #130 | A20718 | 0.4 | 0.4 | 6.3 |
| Pa-17 | " | H6, D114 | | 1.6 | 3.1 | 12.5 |
| Pa-18 | " | H8, D121 | | 1.6 | 0.4 | 3.1 |

TABLE 9-continued

In Vitro Activity By Agar Dilution Technique Against 61 Strains of *Pseudomonas aeruginosa* (Mueller-Hinton Agar)

| BBRI Code # | Organism | | MIC (mcg/ml) BB-P 598 | BB-P 642 | Carben- icillin |
|---|---|---|---|---|---|
| Pa-19 | " | A20229 | 0.8 | 0.8 | 12.5 |
| Pa-20 | " | A20325 | 3.1 | 1.6 | 25 |
| Pa-21 | " | A20601 | 3.1 | 1.6 | 25 |
| Pa-23 | " | A20741 | 3.1 | 1.6 | 25 |
| Pa-24 | " | A20896 | 100 | >100 | >100 |
| Pa-25 | " | A20897 | 1.6 | 1.6 | 3.1 |
| Pa-26 | " | PS32 | 25 | 12.5 | 0.4 |
| Pa-27 | " | GN315 A21294 | 1.6 | 0.8 | 25 |
| Pa-28 | " | C.P.H. 10527/72 | 3.1 | 1.6 | 50 |
| Pa-29 | " | D122 | 3.1 | 1.6 | 25 |
| Pa-30 | " | A20600 | 1.6 | 1.6 | 25 |
| Pa-31 | " | A20594 | 1.6 | 0.4 | 12.5 |
| Pa-32 | " | A20595 | 3.1 | 1.6 | 50 |
| Pa-33 | " | A20598 | 1.6 | 0.8 | 12.5 |
| Pa-34 | " | A20603 | 1.6 | 0.8 | 25 |
| Pa-35 | " | | 6.3 | 3.1 | 100 |
| Pa-36 | " | | <0.2 | 0.8 | 1.6 |
| Pa-37 | " | A20130 | 3.1 | 1.6 | 50 |
| Pa-38 | " | A20349 | 12.5 | 6.3 | 100 |
| Pa-39 | " | A20641 | 1.6 | 0.8 | 12.5 |
| Pa-41 | " | A21227 | 3.1 | 1.6 | 25 |
| Pa-42 | " | A21229 | 6.3 | 12.5 | >100 |
| Pa-43 | " | A21233 | 3.1 | 1.6 | 50 |
| Pa-44 | " | A21274 | 6.3 | 1.6 | 50 |
| Pa-45 | " | GN 4925 | 6.3 | 3.1 | 100 |
| Pa-51 | " | A9910 | 3.1 | 1.6 | 25 |
| Pa-52 | " | A9926 | 3.1 | 3.1 | 50 |
| Pa-53 | " | A20126 | 3.1 | 1.6 | 25 |
| Pa-54 | " | A20128 | 3.1 | 3.1 | 50 |
| Pa-55 | " | A20227 | 3.1 | 3.1 | 50 |
| Pa-56 | " | A20228 | 3.1 | 1.6 | 25 |
| Pa-57 | " | A20546 | 3.1 | 1.6 | 50 |
| Pa-58 | " | A20557 | 6.3 | 3.1 | 50 |
| Pa-59 | " | A20574 | 1.6 | 0.8 | 25 |
| Pa-60 | " | A20602 | 1.6 | 1.6 | 25 |
| Pa-61 | " | A20726 | 3.1 | 3.1 | 50 |
| Pa-62 | " | A21213 | >100 | >100 | >100 |
| Pa-64 | " | A21336 | 1.6 | 0.8 | 25 |
| Pa-65 | " | A21428 | 1.6 | 1.6 | 25 |
| Pa-66 | " | A21434 | 3.1 | 3.1 | 50 |
| Pa-67 | " | A21509 | 6.3 | 3.1 | 50 |
| Pa-68 | " | A21510 | 3.1 | 3.1 | 50 |
| Pa-69 | " | A21587 | 6.3 | 3.1 | 100 |
| Pa-70 | " | K-PS102 (KR-102) | 3.1 | 1.6 | 25 |
| Geometric mean of MIC | | | 3.5 | 2.27 | 29.98 |
| Mean % relative activity | | | 856 | 1319 | 100 |

While, as indicated above, the penicillin derivatives of the present invention are useful antibacterial agents in themselves, they are particularly useful when used in combination with the aminoglycoside antibiotic, amikacin (or a pharmaceutically acceptable acid addition salt thereof), disclosed, for example, in U.S. Pat. No. 3,781,268. In another aspect, therefore, the present invention provides a pharmaceutical composition comprising (A) a penicillin derivative of formula Ia or Ib above, or a pharmaceutically acceptable salt or physiologically hydrolyzed ester thereof as defined above and (B) the aminoglycoside antibiotic, amikacin (1-[L-(—)-γ-amino-α-hydroxybutryl]kanamycin A), or a pharmaceutically acceptable acid addition salt thereof, optionally in admixture with a pharmaceutically acceptable carrier or diluent.

As used herein, the term "pharmaceutically acceptable acid addition salt" used in reference to amikacin refers to those pharmaceutically acceptable acid addition salts disclosed in U.S. Pat. No. 3,781,268 as being included within the scope of the invention claimed therein. Thus, suitable salts of amikacin include mono-, di-, tri- or tetra salts formed with such pharmaceutically acceptable acids as acetic, hydrochloric, sulfuric, maleic, phosphoric, nitric, hydrobromic, ascorbic, malic and citric acids. A most preferred amikacin salt is amikacin disulfate (amikacin sulfate).

Pharmaceutical compositions comprising both a penicillin of formula Ia or Ib (or a pharmaceutically acceptable salt or a physiologically hydrolyzed ester thereof) and amikacin (or a pharmaceutically acceptable acid addition salt thereof) possess many advantages over compositions comprising only one or the other of the two antibiotic components. Thus, a broadened antibacterial spectrum can be achieved since amikacin is antibacterially effective against organisms not affected by the penicillin, and vice versa. The potential nephrotoxicity and ototoxicity problems associated with the aminoglycoside antibiotic can be reduced by administration of a synergistic antibacterial combination product which permits a lower dosage of the aminoglycoside to achieve the same therapeutic effect. Reduced amikacin doses made possible by the synergistic combination product might also allow patients suffering from Pseudomonas infections to be treated with this highly effective antibiotic composition for a longer period of time than currently recommended for amikacin therapy (currently a 15 day limit is recommended).

The therapeutic penicillin-aminoglycoside compositions of the present invention may be administered to mammals, including man, by injection. The compositions may have optionally incorporated therewith standard pharmaceutically acceptable solid or liquid carriers or diluents. Other suitable dosage unit forms may be prepared according to known methods of the pharmaceutical industry.

The relative amount of the active ingredients in the combination according to the present invention may vary between wide ranges depending on the particular organism being treated and the choice of the physician as to whether to favor one or the other of the antibiotic components in treating a particular patient. A preferred weight ratio of the components found to provide synergistic bactericidal results against the four *Pseudomonas aeruginosa* strains mentioned above is between about 1:2 (amikacin:penicillin) and 1:100. Compositions outside of this preferred range also provide advantageous results, however, and are intended to be included within the scope of the present invention. As an example of a proposed human dose, a parenteral preparation may be used comprising 200 mg. amikacin sulfate and 400 mg. a penicillin of formula Ia or Ib. The dry-fill containing the amikacin and pencillin is dissolved in sterile water and then administered by injection as a single dose of the antibiotic combination. This proposed single dose might be administered about twice a day as a proposed daily human dosage. The particular dosage selected will, of course, be determined by the physician after considering the age, weight and condition of the subject and is determinable by those skilled in the art based on data presented herein and experience with other known penicillin-aminoglycoside combinations.

A preferred embodiment of the present invention is a compound of the formula

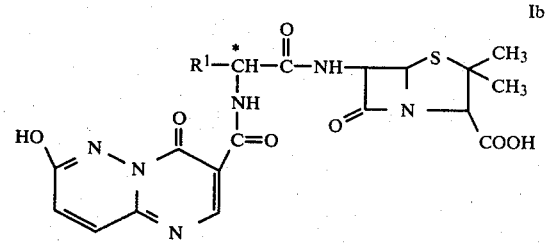

Ib in which R¹ is phenyl or p-hydroxyphenyl, or a pharmaceutically acceptable salt or physiologically hydrolyzed ester thereof.

Another preferred embodiment of the present invention is a pharmacetical composition comprising (A) a compound of the formula

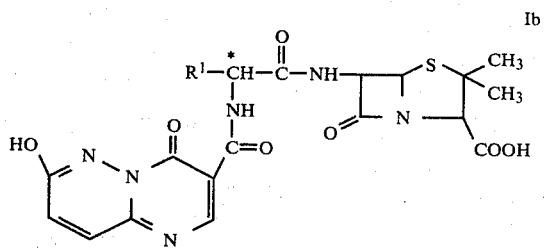

Ib in which R¹ is phenyl or p-hydroxyphenyl, or a pharmaceutically acceptable salt or physiologically hydrolyzed ester thereof and (B) the aminoglycoside antibiotic, amikacin, or a pharmaceutically acceptable salt thereof, optionally in admixture with a pharmaceutically acceptable carrier or diluent.

Also provided by the present invention is a method for the treatment of antibacterial infections, particularly Pseudomonas infections, in mammals, including man, which method comprises administering to a mammal having such an infection an antibacterially-effective dose of a penicillin of formula Ia or Ib, or a pharmaceutically acceptable salt or physiologically hydrolyzed ester thereof. In a more preferred embodiment of said method, the penicillin has the formula Ib in which R¹ is phenyl or p-hydroxyphenyl.

Also provided by the present invention is a method for the treatment of antibacterial infections, particularly Pseudomonas infections, in mammals, including man, which method comprises administering to a mammal having such an infection an antibacterially-effective dose of a pharmaceutical composition comprising (A) a penicillin of formula Ia or Ib, or a pharmaceutically acceptable salt or physiologically hydrolyzed ester thereof and (B) the aminoglycoside antibiotic, amikacin, or a pharmaceutically acceptable salt thereof, optionally in admixture with a pharmaceutically acceptable carrier or diluent. In a more preferred embodiment, the penicillin has the formula Ib in which R¹ is phenyl or p-hydroxyphenyl.

Also included within the present invention are pharmaceutical compositions comprising a mixture of an antibacterially effective amount of a compound of formula Ia or Ib and another semisynthetic penicillin or a cephalosporin or a cephamycin or a β-lactamase inhibitor.

Further details of the present invention are to be found in the following illustrative examples which are not intended to limit the scope of the invention.

Preparation of Starting Materials

The starting acylating agent of formula III may be prepared according to the following reaction scheme. Illustrated here is the preparation of the acylating agent III in the form of its acid chloride.

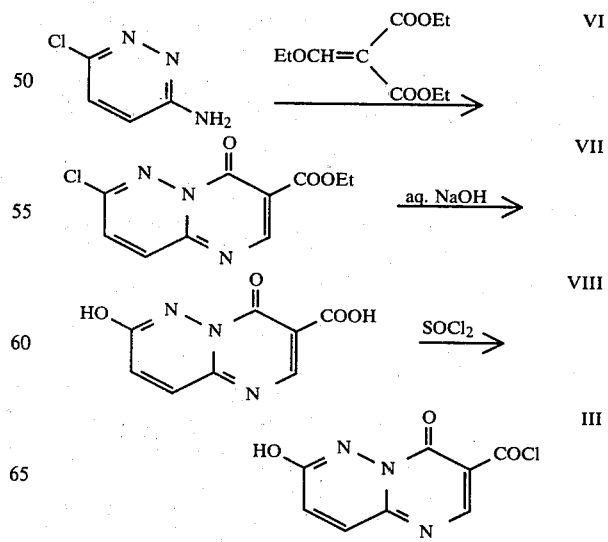

(a)

3-Ethoxycarbonyl-7-chloro-4-oxo-4H-pyrimido-[1,2-b]pyridazine (VII)

A mixture of 3-chloro-6-aminopyridazine [J. Druey et al., Helv. Chim. Acta., 37, 121 (1954)] (8.20 g, 63.56 m mol) and ethyl ethoxymethylenemalonate (15.0 g, 69.4 m mol) in diphenyl ether (70 ml) was heated to distil out ethanol produced. After cooling, the mixture was diluted with n-hexane (300 ml) to precipitate the crude title product, which was dissolved in chloroform (200 ml), treated with a small amount of carbon and evaporated under reduced pressure to 50 ml. The residual solution was diluted with n-hexane (200 ml) to precipitate pure title product. Yield, 7.73 g (56%), M.p. 149°–152° C.

ir: $\nu_{max}^{KBr}$ 1755, 1485, 1295, 1140, 1100 cm$^{-1}$.

uv: $\lambda_{max}^{EtOH}$ 253 nm ($\epsilon$10000), 262 nm ($\epsilon$8200, sh), 348 nm ($\epsilon$8400)

nmr: $\delta_{ppm}^{DMSO-d_6}$ 1.30 (3H, t, 7 Hz, C$\underline{H}_3$), 4.26 (2H, q, 7 Hz, C$\underline{H}_2$), 7.95 (1H, d, 10 Hz, pyridazine-H), 8.15 (1H, d, 10 Hz, pyridazine-H), 8.73 (1H, s, pyrimidine-H).

Anal. Calcd. for $C_{10}H_8N_3O_3Cl$: C, 47.35; H, 3.18; N, 16.57; Cl, 13.08.

Found: C, 47.20, 7.19; H, 2.89, 2,92; N, 16.66, 16.71; Cl, 13.92, 13.92.

(b)

3-Carboxyl-7-hydroxy-4-oxo-4H-pyrimido-[1,2-b]pyridazine (VIII)

A mixture of the product of step (a) (2.53 q, 10 m mol) and 0.5 N NaOH (40 ml) was stirred for 1 hour at room temperature, treated with a small amount of carbon and filtered. The filtrate was acidified to pH 1 with dilute HCl. The precipitated crude product was collected by filtration, crystallized from water (200 ml), collected by filtration, washed with water and dried. Yield 168 mg (7.5%). M.p. 305°–310° (dec.).

ir: $\nu_{max}^{KBr}$ 3560, 3480, 3100–2200, 1730, 1540, 1430, 1350, 1240 cm$^{-1}$.

uv: $\lambda_{max}^{1\%NaHCO_3}$ 236 nm ($\epsilon$12500), 281 nm ($\epsilon$18000), 354 nm ($\epsilon$5700).

nmr: $\delta_{ppm}^{DMSO-d_6}$ 7.45 (1H, d, 10 Hz, pyridazine-H), 7.97 (1H, d, 10 Hz, pyridazine-H), 8.73 (1H, s, pyrimidine-H).

Anal. Calcd. for $C_8H_5N_3O_4.1/2H_2O$: C, 44.45; H, 2.80; N, 19.44.

Found: C, 44.74, 44.55; H, 2.36, 2.46; N, 19.58, 19.59.

(c)

3-Chlorocarbonyl-7-hydroxy-4-oxo-4H-pyrimido-[1,2-b]pyridazine (III)

A mixture of the product of step (b) (380 mg) and thionyl chloride (10 ml) containing one drop of DMF was heated under reflux for 1 hour. The excess thionyl chloride was removed under reduced pressure and the residue was triturated with dry ether. The product was collected by filtration and dried. Yield 346 mg (84%).

ir: $\nu_{max}^{nujol}$ 1760, 1230, 980 cm$^{-1}$.

EXAMPLES

EXAMPLE 1

Sodium 6-[D-(−)-α-phenyl-α-[7-hydroxy-4-oxo-4H-pyrimido-1,2-b]pyridazin-3-ylcarboxamido)acetamido]penicillanate BB-P598

To a suspension of ampicillin trihydrate (564 mg, 1.4 m mol) in water (10 ml) was added the acid chloride (III, 340 mg, 1.39 m mol) and 1 N NaOH alternatively in portions to maintain the pH of the mixture 8 to 8.5 at 0° to 2° C. After the addition was complete, the mixture was stirred for 30 minutes at 2° to 8° C. and then acidified to pH 1 with dilute HCl. The mixture was extracted with a mixture of AcOEt-n-BuOH (10:1, 2×50 ml). The combined extracts were washed with water, treated with a small amount of carbon and dried. Sodium 2-ethylhexanoate (1 M solution in AcOEt, 1.5 ml) was added to the extract and the resulting precipitate was collected by filtration. Yield, 390 mg (50%), m.p. 260°–270° C. (dec.).

ir: $\nu_{max}^{KBr}$ 3600–3000, 1770, 1670, 1630, 1530, 1450, 1340, 1100 cm$^{-1}$.

uv: $\lambda_{max}^{water}$ 282 ($\epsilon$15500), 317 ($\epsilon$4300, sh), 360 ($\epsilon$6100), 376 nm ($\epsilon$4600, sh).

Anal. Calcd. for $C_{24}H_{21}N_6O_7SNa.4H_2O$: C, 45.57; H, 4.62; N, 13.28; S, 5.06.

Found: C, 46.00, 45.68; H, 4.02, 3.90; N, 12.32, 12.26; S, 4.93, 5.16.

EXAMPLE 2

The general procedure of Example 1 is repeated, except that the ampicillin trihydrate utilized therein is replaced by an equimolar amount of 6-[(1-aminocyclohexyl)carboxamido]penicillanic acid, 6-[α-amino-α-(4-hydroxyphenyl)acetamido]penicillanic acid, 6-[α-amino-α-(3-methyl-4-hydroxyphenyl)acetamido]-penicillanic acid, 6-[α-amino-α-(3-chloro-4-hydroxyphenyl)acetamido]-penicillanic acid, 6-[α-amino-α-(3-methoxy-4-hydroxyphenyl)acetamido]-penicillanic acid, 6-[α-amino-α-(4-hydroxymethylphenyl)acetamido]-penicillanic acid, 6-[α-amino-α-(4-acetoxyphenyl)acetamido]penicillanic acid, 6-[α-amino-α-(1,4-cyclohexadien-1-yl)acetamido]-penicillanic acid, 6-[α-amino-β-(1,4-cyclohexadien-1-yl)propionamido]-penicillanic acid, 6-[α-amino-β-(4-methoxy-1,4-cyclohexadien-1-yl)-propionamido]penicillanic acid, 6-[α-amino-α-(cyclohexen-1-yl)acetamido]penicillanic acid, 6-[α-amino-α-cyclohexylacetamido]penicillanic acid, 6-[α-amino-α-(2-thienyl)acetamido]penicillanic acid and 6-[α-amino-α-(3-thienyl)acetamido]penicillanic acid, respectively, and there is thereby produced sodium 6-{[1-(7-hydroxy-4-oxo-4H-pyrimido[1,2-b]pyridazin-3-ylcarboxamido)cyclohexyl]carboxamido}-penicillanate, sodium 6-{α-(7-hydroxy-4-oxo-4H-pyrimido[1,2-b]-pyridazin-3-ylcarboxamido)-α-(4-hydroxyphenyl)-acetamido}penicillanate,
sodium 6-{α-(7-hydroxy-4-oxo-4H-pyrimido[1,2-b]-pyridazin-3-ylcarboxamido)-α-(3-methyl-4-hydroxyphenyl)-acetamido}penicillanate,
sodium 6-{α-(7-hydroxy-4-oxo-4H-pyrimido[1,2-b]-pyridazin-3-ylcarboxamido)-α-(3-chloro-4-hydroxyphenyl)-acetamido}penicillanate,
sodium 6-{α-(7-hydroxy-4-oxo-4H-pyrimido[1,2-b]-pyridazin-3-ylcarboxamido)-α-(3-methoxy-4-hydroxyphenyl)-acetamido}penicillanate,
sodium 6-{α-(7-hydroxy-4-oxo-4H-pyrimido[1,2-b]-pyridazin-3-ylcarboxamido)-α-(4-hydroxymethyl-phenyl)-acetamido}penicillanate,
sodium 6-{α-(7-hydroxy-4-oxo-4H-pyrimido[1,2-b]-pyridazin-3-ylcarboxamido)-α-(4-acetoxyphenyl-)acetamido}-penicillanate,
sodium 6-{α-(7-hydroxy-4-oxo-4H-pyrimido[1,2-b]-pyridazin-3-ylcarboxamido)-α-(1,4-cyclohexadien-1-yl)-acetamido}penicillanate,
sodium 6-{α-(7-hydroxy-4-oxo-4H-pyrimido[1,2-b]-pyridazin-3-ylcarboxamido)-β-(1,4-cyclohexadien-1-yl)-propionamido}penicillanate,
sodium 6-{α-(7-hydroxy-4-oxo-4H-pyrimido[1,2-b]-pyridazin-3-ylcarboxamido)-β-(4-methoxy-1,4-cyclohexadien-1-yl)propionamido}penicillanate,
sodium 6-{α-(7-hydroxy-4-oxo-4H-pyrimido[1,2-b]-pyridazin-3-ylcarboxamido)-α-(cyclohexen-1-yl)-acetamido}penicillanate,
sodium 6-{α-(7-hydroxy-4-oxo-4H-pyrimido[1,2-b]-pyridazin-3-ylcarboxamido)-α-cyclohexylacetamido}-penicillanate,
sodium 6-{α-(7-hydroxy-4-oxo-4H-pyrimido[1,2-b]-pyridazin-3-ylcarboxamido)-α-(2-thienyl-)acetamido}-penicillanate and
sodium 6-{α-(7-hydroxy-4-oxo-4H-pyrimido[1,2-b]-pyridazin-3-ylcarboxamido)-α-(3-thienyl-)acetamido}-penicillanate, respectively.

EXAMPLE 3

Potassium 6-[D-(−)-α-Phenyl-α-(7-hydroxy-4-oxo-4H-pyrimido[1,2-b]pyridazin-3-ylcarboxamido)acetamido]penicillanate The general procedure of Example 1 is repeated except that the sodium 2-ethylhexanoate utilized therein is replaced by an equimolar amount of potassium 2-ethylhexanoate, and the title product is produced.

EXAMPLE 4

Pivaloyloxymethyl 6-[D-(−)-α-Phenyl-α-(7-hydroxy-4-oxo-4H-pyrimido[1,2-b]pyridazin-3-ylcarboxamido)acetamido]penicillanate The procedure of Example 5 of U.K. Pat. No. 1,267,936 is repeated except that the 6-[2,2-dimethyl-5-oxo-4-(p-hydroxyphenyl)-1-imidazolidinyl]penicillanic acid used therein is replaced by an equimolar amount of 6-[D-(−)-α-phenyl-α-(7-hydroxy-4-oxo-4H-pyrimido[1,2-b]-pyridazin-3-ylcarboxamido)acetamido]penicillanic acid, and the title product is produced.

EXAMPLE 5

Acetoxymethyl 6-[D-(−)-α-Phenyl-α-(7-hydroxy-4-oxo-4H-pyrimido[1,2-b]pyridazin-3-ylcarboxamido)acetamido]penicillanate The general procedure of Example 4 is repeated except that the bromomethyl pivalate utilized therein is replaced by an equimolar amount of bromomethyl acetate, and the title product is produced.

EXAMPLE 6

Methoxymethyl 6-[D-(−)-α-Phenyl-α-(7-hydroxy-4-oxo-4H-pyrimido[1,2-b]pyridazin-3-ylcarboxamido)acetamido]penicillanate The general procedure of Example 4 is repeated except that the bromomethyl pivalate utilized therein is replaced by an equimolar amount of chloromethyl methyl ether, and the title product is produced.

EXAMPLE 7

Phthalidyl 6-[D-(−)-α-Phenyl-α-(7-hydroxy-4-oxo-4H-pyrimido[1,2-b]pyridazin-3-ylcarboxamido)acetamido]penicillanate The general procedure of Example 1(b) of U.K. Pat. No. 1,364,672 is repeated except that the 6-[(D-)-α-aminophenylacetamido]penicillanic acid utilized therein is replaced by an equimolar amount of 6-[D-(−)-α-phenyl-α-(7-hydroxy-4-oxo-4H-pyrimido[1,2-b]pyridazin-3-ylcarboxamido)acetamido]penicillanic acid, and the title product is produced.

EXAMPLE 8

A parenteral preparation having the following composition is prepared:

| | |
|---|---|
| Sodium 6-[D-(-)-α-Phenyl-α-(7-hydroxy-4-oxo-4H-pyrimido-[1,2-b]pyridazin-3-ylcarboxamido)-acetamido]penicillanate | 400 mg. |
| Amikacin sulfate | 200 mg. |

In use, the above preparation is dissolved in sterile water and administered by injection.

EXAMPLE 9

Sodium 6-[D-(−)-α-(4-hydroxyphenyl)-α-(7-hydroxy-4-oxo-4H-pyrimido[1,2-b]pyridazin-3-ylcarboxamido)-]-penicillanate (BB-P642)

To a stirred solution of amoxicillin trihydrate (0.84 g, 2.0 m mol) and triethylamine (0.84 ml, 6 m mol) in dry dimethylformamide (10 ml) was added 7-hydroxy-4-oxo-4H-pyrimido[1,2-b]pyridazin-3-ylcarbonyl chloride (0.42 g, 1.9 m mol) at 0° to 5° C. The mixture was then stirred for 1 hour at room temperature and poured into ice-water (100 ml). The mixture was acidified to pH 2 with dilute HCl and extracted with ethyl acetate-n-butanol (10:1, 100 ml×2). The combined extracts were washed with water, treated with a small amount of carbon and dried. One ml of 1 M sodium 2-ethylhexanoate in ethyl acetate was added to the filtrate and the mixture was concentrated under reduced pressure to about one half the volume. The precipitate was collected by filtration, washed with ethyl acetate and dried. Yield, 170 mg (16%). M.p. 250°–260° (dec).

ir: $\nu_{max}^{KBr}$ 3600–3000, 1765, 1665, 1630, 1520, 1450, 1340, 1270 cm$^{-1}$.

uv: $\lambda_{max}^{Buffer\ (pH7)}$ 235 nm (sh, ε, 15600), 282 nm (ε, 17000), 360 nm (ε, 5900), 375 nm (sh, ε, 5000).

nmr: $\delta_{ppm}^{D2O}$ 1.42 (3H, s, Me), 1.45 (3H, s, Me), 4.12 (1H, s, 3-H), 5.35 (3H, s, 5—H, 6—H & α—CH), 6.5–7.6 (6H, m, pyridazine-H & phenyl-H), 8.62 (1H, s, pyrimidine-H).

Analysis: Calcd. for $C_{24}H_{21}N_6O_8SNa\ 3/2\ H_2O$: C, 46.38; H, 4.22; S, 5.16.

Found: C, 46.82, 46.57; H, 4.33, 4.25; S, 4.76.

We claim:

1. A compound having the formula

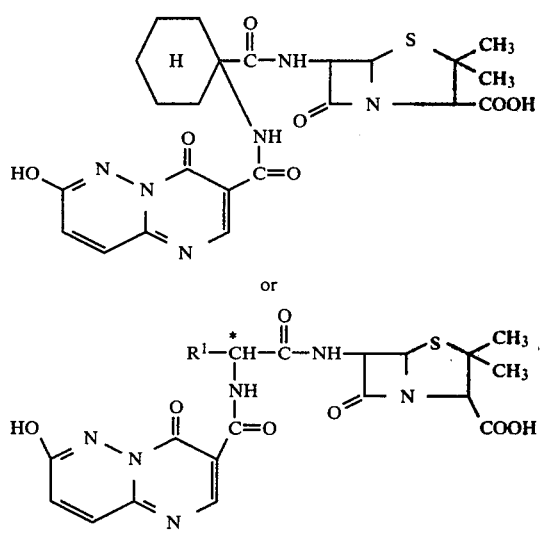

in which R$^1$ is

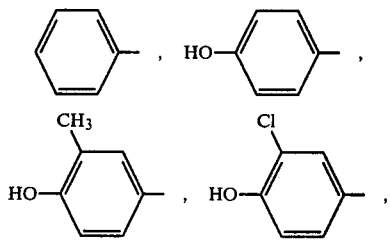

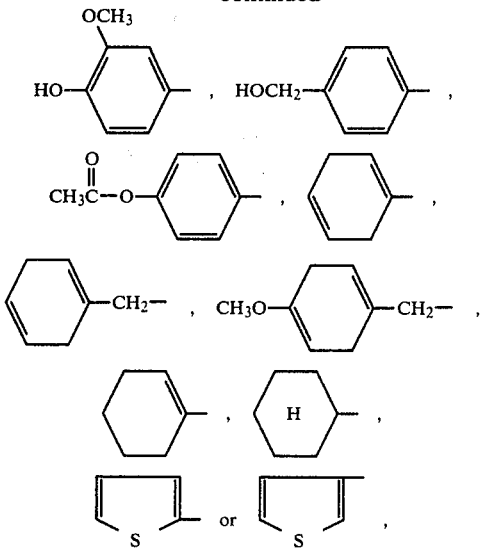

or a pharmaceutically acceptable salt or conventional physiologically hydrolyzed ester thereof.

2. A compound of claim 1 having the structure Ib and having the D-configuration in the 6-side chain, or a pharmaceutically acceptable salt or conventional physiologically hydrolyzed ester thereof.

3. 6-[D-(—)-α-Phenyl-α-(7-hydroxy-4-oxo-4H-pyrimido[1,2-b]pyridazin-3-ylcarboxamido)acetamido]-penicillanic acid.

4. The sodium salt of the compound of claim 3.

5. The potassium salt of the compound of claim 3.

6. The pivaloyloxymethyl ester of the compound of claim 3.

7. The acetoxymethyl ester of the compound of claim 3.

8. The methoxymethyl ester of the compound of claim 3.

9. The phthalidyl ester of the compound of claim 3.

10. 6-[D-(—)-α-(4-Hydroxyphenyl)-α-(7-hydroxy-4-oxo-4H-pyrimido[1,2-b]pyridazin-3-ylcarboxamido)acetamido]-penicillanic acid.

11. The sodium salt of the compound of claim 10.

12. The potassium salt of the compound of claim 10.

13. The pivaloyloxymethyl ester of the compound of claim 10.

14. The acetoxymethyl ester of the compound of claim 10.

15. The methoxymethyl ester of the compound of claim 10.

16. The phthalidyl ester of the compound of claim 10.

* * * * *